United States Patent [19]

Bay

[11] Patent Number: 4,833,250

[45] Date of Patent: May 23, 1989

[54] PROCESS OF CONVERTING A CARBOXYLIC ACID OR CARBOXYLIC ACID HALIDE GROUP TO A TRIHALOMETHYL GROUP

[75] Inventor: Elliott Bay, Ridgefield, Conn.

[73] Assignee: ICI Americas Inc., Wilmington, Del.

[21] Appl. No.: 166,715

[22] Filed: Mar. 24, 1988

Related U.S. Application Data

[63] Continuation-in-part of Ser. No. 37,741, Apr. 13, 1987, abandoned, and a continuation-in-part of Ser. No. 90,171, Aug. 23, 1987, abandoned, which is a continuation-in-part of Ser. No. 23,181, Mar. 9, 1987, abandoned, which is a continuation-in-part of Ser. No. 880,469, Jun. 30, 1986, Pat. No. 4,739,057.

[51] Int. Cl.$^4$ ............................................. C07D 213/02
[52] U.S. Cl. ..................................... 546/345; 570/127; 570/182
[58] Field of Search ................. 546/345; 570/127, 182

[56] References Cited

U.S. PATENT DOCUMENTS 4,419,514 12/1983 McKendry et al. ................. 544/334
4,634,771 1/1987 Shim et al. ........................... 546/286

Primary Examiner—Mary C. Lee
Assistant Examiner—J. Richter
Attorney, Agent, or Firm—Joel G. Ackerman

[57] ABSTRACT

Carboxylic acid or carboxylic acid halide groups on aryl or heterocyclic aryl rings are directly converted to trihalomethyl groups by using a phenylhalophosphorane, optionally generated in situ by reaction of a phenylphosphonous halide and chlorine.

8 Claims, No Drawings

PROCESS OF CONVERTING A CARBOXYLIC ACID OR CARBOXYLIC ACID HALIDE GROUP TO A TRIHALOMETHYL GROUP

This application is a continuation-in-part of U.S. Ser. Nos. 37,741, filed Apr. 18, 1987 now ABN and 90,171, filed Aug. 23, 1987, now ABN, both of which are continuations-in-part of U.S. Ser. No. 23,181, filed Mar. 9, 1987, now ABN, which in turn is a continution-in-part of U.S. Ser. No. 880,469, filed June 30, 1986 now U.S. Patent 4739057.

BACKGROUND OF THE PRESENT INVENTION

1. Field of the Present Invention

The present invention relates to a method for converting a carboxylic acid or carboxylic acid halide group to a trihalomethyl group.

2. Description of the Prior Art

U.S. Pat. No. 4,419,514, McKendry, teaches that carboxylic acid groups on aryl or heteroaryl rings can be converted to trichloromethyl groups if contacted with a mixture of phenylphosphonic dichloride ($C_6H_5P(O)Cl_2$) and phosphorus pentachloride.

DESCRIPTION OF RELATED DEVELOPMENT

More recently, U.S. Pat. No. 4,634,771, Shim et al., proposed a similar conversion by using a mixture of phenylphosphonous dichloride ($C_6H_5PCl_2$), phosphorus trichloride and chlorine. This particular process was found by the present inventor to give a good yield of crude product. However, when attempts were made to distill the crude reaction product obtained using the Shim et al. procedure, a reddish residue remained in the distillation vessel which produced a lower than anticipated yield of the desired end product. Apparently, the reaction mixture obtained by Shim et al. contained undesired by-products that had not been fully characterized by those investigators, which precluded the obtaining of the desired level of yield of final product when the reaction product mixture was distilled.

SUMMARY OF THE PRESENT INVENTION

The present invention is an improvement in the Shim et al. procedure which results in yields of distilled product from the reaction product mixture which are higher than obtainable using the Shim et al. process. The present process relies upon the use of a phenylhalophosphorane chlorinating agent to convert a carboxylic acid or carboxylic acid halide group on an aryl or heterocyclic aromatic ring to a trihalomethyl group. If desired, the phenylhalophosphorane chlorinating agent can be generated in situ by use of a phenylphosphonous chlorinating agent (phenylphosphonous dihalide and halogen). No addition of phosphorus trihalide is used in the present process.

DETAILED DESCRIPTION OF THE PRESENT INVENTION

The present invention is directed to conversion of one or more carboxylic acid or carboxylic acid halide groups on an aryl or heterocyclic aromatic ring to a trihalomethyl group or groups. Representative heterocyclic compounds are based on N-heteroaromatic structures, such as pyridine ring compounds. The carboxylic acid or carboxylic acid halide moiety can include one or two such groups in non-sterically hindered ring positions (e.g., in non-adjacent positions.) If desired, the carboxylic starting compounds can be additionally substituted with sterically compatible, non-interfering substituents such as halogen (chloro, fluoro), nitro, cyano, alkyl, alkoxy, aryl, alkyl-substituted aryl, alkoxy-substituted aryl, aryloxy, and/or trihalomethyl.

The chlorinating agent of the present invention is a phenylchlorophosphorane chlorinating agent, preferably $C_6H_5PCl_4$. In its broadest context, the phenylchlorophosphorane chlorinating agent used herein includes those phenylchlorophosphorane compounds having a sufficient number of chloro groups (e.g., from 2-4) to achieve the desired chlorination reaction. The molar ratio of this chlorinating agent to carboxylic acid starting material may range from about 2:1 to about 3:1. The reaction is conducted at temperatures of from about 110° C. to about 180° C. in a solvent medium of phenylphosphonic dichloride. The phosphorane chlorinating agent can have its ring substituted with electron withdrawing groups such as fluoro, nitro and the like.

If desired, the phenylchlorophosphorane chlorinating agent of the present invention can be generated in situ by reaction of a phenylphosphonous halide and chlorine.

The product of such reaction, between a carboxylic acid group and a phenylchlorophosphorane chlorinating agent, is a trichloromethyl group.

In accordance with another aspect of this invention, trihalomethyl groups can be obtained by conversion of a carboxylic acid halide group with a phenylchlorophosphorane chlorinating agent. The carboxylic acid halide compound may be used as the starting material in this process or it may be obtained by conversion of a carboxylic acid group with a suitable chlorinating agent, e.g., phosgene, thionyl halides, etc., as known. The resulting acid halide, when reacted with a suitable amount of phosphorane chlorinating agent (e.g., in a molar ratio of about 1:1 to 3:1) results in the desired trihalomethyl groups by conversion of the carbonyl linkage between the ring and the acid halide atom. If desired, the phosphorane chlorinating agent can be generated in situ by reaction of chlorine and phenylphosphonous halide as earlier described.

Reaction of a phenylchlorophosphorane chlorinating agent with a carboxylic acid chloride produces a trichloromethyl group. In another embodiment of this invention, a mixed halogen trihalomethyl group, e.g., a dichlorohalomethyl group in which the third halogen is other than chloro, can be obtained. This is performed by reacting a phenylchlorophosphorane chlorinating agent with an acid halide group in which the halogen is other than chloro; i.e., with an acid bromide or fluoride. Acid halides of this type may be obtained by conventional means, for instance, reacting the corresponding carboxylic acid chloride with hydrogen fluoride, producing the carboxylic acid fluoride. The carboxylic acid halide (nonchloride type) can be reacted with the phenylchlorophosphorane under the previously described conditions to produce a dichlorohalo (e.g., dichlorofluoro)methyl group.

For example, 6-hydroxynicotinic acid can be reacted with thionyl chloride in the conventional manner, producing 6-chloronicotinic acid chloride. This can then be reacted with hydrogen fluoride, producing 6-chloronicotinic acid fluoride, which can be then reacted with a phenylchlorophosphorane as described above to produce 2'-chloro-5-dichlorofluoromethylpyridine.

The present invention is further illustrated by the examples which follow.

EXAMPLE 1

Nicotinic acid [225 grams (g), 1.83 moles] was added in one portion to a solution of phenylphosphonic dichloride [600 milliliters (ml)] and phenylphosphonous dichloride (655 g, 3.66 moles) in a 3-liter, 4-necked, round-bottom flask fitted with an overhead stirrer, reflux condenser, thermocouple, and gas inlet tube. Chlorine gas (260 g, 3.66 moles) was metered into the reaction mixture below the surface of the solution. The chlorine was added at the rate of about 4.5 g per minute. The phenylphosphonous dichloride and chlorine react to form phenyltetrachlorophosphorane in situ. An ice bath was placed on the reaction setup to keep the temperature below 90° C. After all the chlorine was added, the milky white slurry was heated to 170° C. for 4 hours. During this time the solution became a clear dark red. The stirrer was stopped, and the reaction mixture was allowed to cool and stand at room temperature under a nitrogen atmosphere.

The reaction mixture from the preceding step was a solid orange mass of crystals after standing at room temperature over a weekend. The thermocouple was removed and the solids were broken up into a fine slurry by mechanical stirring. Hexane (500 ml) was added to aid in breaking up the slurry. The mixture was stirred at room temperature for 30 minutes. The solid product was filtered out through a sintered glass filter and was dried in a vacuum desiccator. The product (407.6 g) was the hydrochloride salt of 3-trichloromethylpyridine and was a light yellow-orange solid. The yield was calculated as 96%.

The filtrate containing the phenylphosphonic dichloride and the hexane was distilled. The hexane was removed at 460 mm Hg giving a head temeprature of about 50°–55° C. The vacuum was then lowered to 6 mm/Hg giving a phenylphosphonic dichloride boiling at 110°–119° C. A total of 1526 g of phenylphosphonic dichloride was recovered. The calculated amount of phenylphosphonic dichloride present was 1538.5 g, giving a recovery of 99%.

EXAMPLE 2

The phenylphosphonic dichloride recovered in Example 1 (400 ml) was mixed with 875 g (4.89 moles) of phenylphosphonous dichloride in a 3-liter, 4-necked flask fitted with an overhead stirrer, condenser, thermocouple, and chlorine inlet tube. To this solution nicotonic acid (300 g, 2.44 moles) was added in one portion. The temperature in the reactor pot rose about 10° to about 35° C. during this addition. An ice bath was placed around the reactor flask, and chlorine (347 g, 4.89 moles) was added just below the surface of the slurry at the rate of 4 g per minute. The reaction mixture was a white slurry that was noticeably thicker after the first 30 minutes of chlorine addition. The temperature continued to climb and the slurry thinned out a little. The reactor reached a temperature of about 68°–70° C. when about one-half of the chlorine was added (about 50 minutes into the chlorine addition). Thereafter, the temperature began falling to about 50°–55° C. The ice bath was lowered and the temperature began to slowly climb. The last 30 g of chlorine was added at a rate slower than 4 g per minute in order to have it absorbed by the reaction mixture. After all the chlorine had been added, the heating mantle was placed on the flask, and the reaction mixture was slowly heated to 140° C. over a period of about 1.5 hours. The slurry continued to thin out during this time. The reaction mixture became a clear light orange color aftr 1 hour at 140° C. The mixture was heated with stirring for another 1.5 hours. The heating mantle was removed and the reaction mixture allowed to cool to 70° C. A water bath was placed on the reaction, and the mixture was cooled to 55° C. Seed crystals were added and as soon as crylstals started forming, 250 ml of hexane was added. The slurry was allowed to cool without the water bath with stirring overnight.

The room temperature reaction slurry was then poured in one portion into a 3000 ml, coarse sintered glass funnel. The phenylphosphonic dichloride and and hexanes were removed by vacuum filtration. The product was slurried with 500 ml of hexane in a filter funnel and this hexane portion was removed by vacuum filtration. The off-white product was dried in a vacuum desiccator. Approximately 444.1 g of materials was obtained after drying, giving a crude yield of 78%. The product was the hydrochloride salt of 3-trichloromethylpyridine.

Sodium carbonate (70 g, 0.66 mole) was added slowly to 200 g (0.86 mole) of the above-described pyridinium salt dissolved in 500 ml of water and 200 ml of methylene chloride. After carbon dioxide evolution stopped, the slurry was filtered to remove any solid nicotinic acid, and the water layer was separated with a separatory funnel. The methylene chloride layer was dried using magnesium sulfate and the resulting material was rotary concentrated giving 137.4 g of a clear yellow liquid product (81% yield) which was judged to be 98% pure by VPC analysis.

EXAMPLE 3

This example shows another procedure wherein the pyridinium salt was reacted with sodium carbonate to form the desired product.

The hydrochloride salt of 3-trichloromethylpyridine (650 g, 2.79 moles) was mixed with 650 ml of methylene chloride and 600 ml of water. To this slurry was slowly added 230 g of sodium carbonate (2.17 moles) dissolved in 1000 ml of water. The mixture was rapidly stirred during the addition and much carbon dioxide was evolved. The mixture was transferred to a large separatory funnel and the organic layer was removed. This layer was washed once with water and dried using magnesium sulfate. The solvent was removed by rotary concentration. Vacuum distillation at 78°–80° C. and 0.5 mm Hg gave 430.5 g of the desired 3-trichloromethylpyridine product (79% yield).

EXAMPLE 4

Phenylphosphonic dichloride (1600 ml) and phenylphosphonous dichloride (3500 g, 19.55 moles) were mixed in a 12-liter, 4-necked flask fitted with a reflux condenser, nitrogen atomsphere inlet, overhead stirrer, thermocouple, and chlorine inlet tube. The flask was in an ice bath. Nicotinic acid (1200 g, 9.76 moles) was added in one portion with stirring and a small temperature increase of about 10° C. was observed. Chlorine (1388 g, 19.55 moles) was then added through a tube immersed below the surface of the solution at the rate of about 4 g per minute. After addition of the chlorine, the reaction mixture was allowed to stand at room temperature overnight.

The reaction mixture was then heated with stirring to 130° C. and was maintained at that temperature for about 5 hours. The heating mantle was removed, and the reaction was allowed to cool to 55° C. Seed crystals of product (the hydrochloride salt of 3-trichloromethylpyridine) were added along with 2000 ml of hexane. The pyridinium salt product crystallized, and the resulting slurry was cooled to room temperature. The product was filtered and washed with hexane. The product was placed in a large filter flask which was attached to a vacuum line to remove any residual hexanes from the product. The weight of vacuum dried product was 2076 g for a yield of 91%.

EXAMPLE 5

The 3-trichloromethylpyridinium hydrochloride salt (2836 g, 12.17 moles) was placed in a 22-liter pot with 2800 ml of methylene chloride and 2600 ml of water. A solution of 1000 g of sodium carbonate in 4300 ml of water was then added slowly so that the gassing could be controlled. The temperature was maintained with an ice bath between 15°–20° C. The lower organic phase was then separated and was dried with magnesium sulfate. The mixture was filtered and the methylene chloride was removed by rotary evaporation. The concentrated material was distilled at 77°–79° C. and 0.5 mm Hg giving 1918 g of the desired 3-trichloromethylpyridine product. The yield was 80%.

EXAMPLE 6

This example illustrates the use of this invention to produce a mixed halogen trihalomethyl group from a carboxylic acid halide.

(a) A solution of thionyl chloride (149 g, 1.25 moles) and a catalytic amount of N,N-dimethylformamide (1 g, 0.14 mole) were placed in a 500 ml 4-neck flask fitted with an overhead stirrer, reflux condenser, thermometer and solids additional funnel. This solution was heated with stirring to 60° C. and the solid 6-hydroxynicotinic acid (69.5 g, 0.5 mole) was added portionwise from the solids addition funnel. After the addition was complete, the reaction mixture was heated to 85° C. over a two hour period. At this point, gas evolution had nearly stopped, and the reaction mixture was cooled under a nitrogen atmosphere. The reaction mixture was then transferred to a still pot, and the excess thionyl chloride was distilled at atmospheric pressure. The residue was vacuum distilled giving 88.2 g of 6-chloronicotinic acid chloride (b.p.: 68°–71° C./0.5 mmHg) as an oil that solidified upon standing. The yield was 86%.

(b) The following reaction was conducted under a nitrogen atmosphere. The off gases from the reaction were vented to a caustic scrubber.

6-Chloronicotinic acid chloride (65.7 g, 0.37 mole) from step (a) was placed in a 125 ml Teflon® fluorocarbon polymerlined flask fitted with an ice water cooled Teflon® polymer-lined condenser and a magnetic stirrer. Anhydrous hydrogen fluoride (14 g, 0.70 mole) was condensed into the reaction flask through the condenser. The reaction mixture was warmed with a water bath, and the contents of the flask liquified with the evolution of hydrogen chloride. The condenser was removed when the evolution of hydrogen chloride ceased. The reaction mixture was warmed to a temperature of 100° C., and the excess hydrogen fluoride was vented to the scrubber. The reaction product solidified upon cooling. The only material present (by vapor phase chromatography (VPC) analysis) was 6-chloronictonic acid fluoride.

(c) 6-Chloronicotinic acid fluoride (60 g, 0.38 mole) from step (b) was melted and added in one portion to a 500 ml, 4-neck flask containing phenylphosphonic dichloride (70 ml). The reaction flask was fitted with an overhead stirrer, thermometer and reflux condenser. The reaction was carried out under a nitrogen atmosphere. Phenylphosphonous dichloride (69 g, 0.39 mole) was then added to the reaction mixture. The flask was fitted with a gas inlet tube, and chloride gas (28 g, 0.39 mole) was bubbled into the stirred reaction mixture. The chlorine was added at the rate of 1 g/minute. The temperature of the reaction was kept below 35° C. with an ice bath during the chlorine addition. The ice bath was replaced with a heating mantle when the chlorine addition was complete, and the reaction was heated to a temperature of 130° C. overnight. The reaction mixture was cooled and was analyzed. The reaction was found to be 6% unreacted starting material along the 25% 2-chloro-5-trichloromethylpyridine, 32% 2-chloro-5-dichlorofluoromethylpyridine (the desired product) and 37% 6-chloronicotinic acid chloride.

EXAMPLE 7

This example illustrates the use of this invention to produce 2-chloro,5-trichloromethylpyridine.

In a flask were mixed 6-chloronicotinic acid (30 g, 0.19 mole), phenylphosphonous dichloride (69 g, 0.39 mole), and phenylphosphonic dichloride (70 ml). The mixture was stirred while chlorine (28 g, 0.39 mole) was bubbled in at 2 g/min. The temperature rose to 90° C. and was maintained during chlorine addition at 90°–100° C. using an ice bath. After the chlorine addition was complete the mixture was then heated and maintained at 130°–140° C. for 4 hours. VPC analysis indicated the presence of some starting material; heating was then continued for an additional 18 hours at 150° C. Attempts to vacuum distill off the phenylphosphonic dichloride resulted in codistillation of this compound and the reaction product.

The distilled reaction mixture was slowly added to diulte hydrochloric acid. The temperature rose to 80° C.; ice was then added until the solution was at a temperature of 25° C. Then, portions of sodium carbonate were added until the solution was basic. It was then extracted with methylene chloride; the combined extracts were washed with water, dried over magnesium sulfate and evaporated. The last traces of methylene chloride were removed by a vacuum pump. There was obtained 20 g of a white solid, melting point 47°–49° C., which was identified as the desired product by NMR spectroscopy.

The foregoing examples should not be construed in a limiting sense since they are only intended to be illustrative of certain embodiments of the claimed invention. The scope of protection that is claimed is set forth in the claims which follow.

What is claimed is:

1. A process of converting a carboxylic acid or carboxylic acid halide group on the ring of an aryl or heterocyclic aromatic compound to a trihalomethyl group which comprises contacting such compound with a phenylchlorophosphorane chlorinating agent.

2. A process according to claim 1 wherein the chlorinating agent is generated in situ by reaction of a phenylphosphonous dihalide and chlorine.

3. A process according to claim 1 wherein the compound contains a carboxylic acid group and the product contains a trichloromethyl group.

4. A Process according to claim 1 wherein the compound contains a carboxylic acid chloride group and the product contains a trichloromethyl group.

5. A process according to claim 1 wherein the compound contains a carboxylic acid bromide or fluoride group and the product contains a dichlorobromomethyl or dichlorofluoromethyl group, respectively.

6. A process according to claim 1 wherein the phenylchlorophosphorane chlorinating agent has the formula $C_6H_5PCl_4$.

7. A process according to claim 1 wherein the aromatic compound is a pyridine compound.

8. A process according to claim 1 wherein the phenylchlorophosphorane chlorinating agent contains 2 to 4 chlorine atoms.

* * * * *